US008625098B2

(12) United States Patent
Li et al.

(10) Patent No.: US 8,625,098 B2
(45) Date of Patent: Jan. 7, 2014

(54) SYSTEM AND METHOD FOR REAL-TIME MEASUREMENT OF EQUIVALENCE RATIO OF GAS FUEL MIXTURE

(75) Inventors: Hejie Li, Clifton Park, NY (US); Shawn David Wehe, Niskayuna, NY (US); Keith Robert McManus, Clifton Park, NY (US)

(73) Assignee: General Electric Company, Niskayuna, NY (US)

(*) Notice: Subject to any disclaimer, the term of this patent is extended or adjusted under 35 U.S.C. 154(b) by 234 days.

(21) Appl. No.: 12/971,154

(22) Filed: Dec. 17, 2010

(65) Prior Publication Data

US 2012/0154813 A1    Jun. 21, 2012

(51) Int. Cl.
G01N 21/00    (2006.01)
G01J 3/433    (2006.01)
G01N 21/39    (2006.01)

(52) U.S. Cl.
CPC ........... *G01J 3/433* (2013.01); *G01N 21/39* (2013.01)
USPC ........................................................ 356/437

(58) Field of Classification Search
None
See application file for complete search history.

(56) References Cited

U.S. PATENT DOCUMENTS

| | | | | |
|---|---|---|---|---|
| 5,042,905 A | * | 8/1991 | Anjan et al. | 385/13 |
| 5,659,133 A | * | 8/1997 | Sims et al. | 356/43 |
| 6,318,891 B1 | | 11/2001 | Haffner et al. | |
| 7,248,357 B2 | * | 7/2007 | Servaites et al. | 356/306 |
| 7,248,755 B2 | * | 7/2007 | Sappey et al. | 385/13 |
| 7,969,576 B1 | * | 6/2011 | Buckley et al. | 356/437 |
| 2008/0076080 A1 | | 3/2008 | Hu et al. | |
| 2008/0299505 A1 | | 12/2008 | Winklhofer | |
| 2009/0141349 A1 | | 6/2009 | Myhre | |
| 2009/0180939 A1 | * | 7/2009 | Hagen et al. | 422/194 |
| 2009/0234555 A1 | * | 9/2009 | Williams et al. | 701/100 |
| 2010/0103424 A1 | | 4/2010 | Davis, Jr. et al. | |

FOREIGN PATENT DOCUMENTS

| | | |
|---|---|---|
| FR | 2816056 A1 | 5/2002 |
| JP | 2004204787 | 7/2004 |
| JP | 2005226893 A | 8/2005 |
| WO | 2007087081 | 8/2007 |

OTHER PUBLICATIONS

Silver et al., Diode Laser Measurement of Concentration and Temperature in microgravity combustion, 1999, Meas. Sci. Technol. 10, pp. 845-852.*

Quang-Viet Nguyen, Rajiv K. Mongia and Robert W. Dibble; "Real-time optical fuel-to-air ratio sensor for gas turbine combustors"; NASA/TM—1999-20904; Mar. 1999; 12 Pages.

(Continued)

*Primary Examiner* — Gregory J Toatley
*Assistant Examiner* — Juan D Valentin, II
(74) *Attorney, Agent, or Firm* — Joseph J. Christian

(57) ABSTRACT

A real-time monitoring of an equivalence ratio of a gas-fuel mixture of a gas turbine engine is provided. The system includes multiple optical probes arranged on a plurality of fuel nozzles for transmitting laser beams directly through a gas-fuel mixture or indirectly by reflecting the laser beams from a surface of a centerbody or burner tube of the fuel nozzle. The system also includes one or more detectors to measure the transmitted laser beams from the multiple optical probes. Further, the system includes a data acquisition subsystem for acquiring and processing signals from the one or more detectors to determine the equivalence ratio of the gas-fuel mixture of the nozzle.

21 Claims, 14 Drawing Sheets

(56) References Cited

OTHER PUBLICATIONS

Javier Ballester, Ana Sanz, Ricardo Hernández, and Andrzej Smolarz; "Optical sensors monitor flames"; 2006 SPIE—The International Society for Optical Engineering; 2 Pages.

K.M. Hinckley, A.J. Dean; "Time-Resolved Measurements of Fuel-Air Stoichiometry in Pulse Detonation Engines Using a Non-Intrusive Laser Sensor": 2004GRC509, Jan. 2005, Public (Class 1); Technical Information Series; 11 Pages.

E Tomita et al; "In situ measurement of hydrocarbon fuel concentration near a spark plug in an engine cylinder using the 3.392 μm infrared laser absorption method: discussion of applicability with a homogeneous methane-air mixture"; Institute of Physics Publishing, Measurement Science and Technology 14 (2003) 1350-1356.

* cited by examiner

SYSTEM AND METHOD FOR REAL-TIME MEASUREMENT OF EQUIVALENCE RATIO OF GAS FUEL MIXTURE

BACKGROUND

The invention relates generally to determining equivalence ratio of a gas-fuel mixture and more particularly to a system and method of measuring an equivalence ratio of the gas-fuel mixture in a gas turbine engine in real time.

In order to reduce $NO_x$ emissions and increase lifetime for gas turbine engines for power and propulsion systems, a lean premixed combustion is widely preferred. In lean flames, the dominant $NO_x$ formation mechanisms depend on the local flame temperature. The gas turbine engines that operate at lean fuel/air equivalence ratios significantly reduce $NO_x$ production due to lower flame temperatures. In addition, lower flame temperatures reduce maintenance requirements for gas turbine components such as combustion liner. Thus, equivalence ratio is a key parameter for operations of a gas turbine engine. However, the lean premixed combustion is susceptible to thermoacoustic instabilities and lean blowout, thereby, reducing efficiency and increasing emissions. This further leads to hardware damage and causes safety hazards.

Furthermore, thermoacoustic instability is a self-sustained combustion oscillation near the acoustic frequency of the combustion chamber, which is the result of the closed loop coupling of unsteady heat release to pressure oscillations. Intensive experimental and theoretical work has been performed to understand the driving mechanisms of thermoacoustic instabilities, and to suppress these instabilities in laboratory-scale and full-scale combustors. It is well understood that heat release fluctuations can produce pressure oscillations; however, the mechanisms whereby pressure oscillations result in heat release fluctuations are not well known. Equivalence ratio fluctuation is considered to be one of the most important driving mechanisms for thermoacoustic instabilities in fuel-lean gas turbine combustion systems. Because of the complex physical and chemical interactions involved in thermoacoustic oscillations, it is difficult to predict this unstable combustion behavior. Therefore, measurement of the equivalence ratio fluctuation during unstable combustion is of great importance for monitoring thermoacoustic instabilities in the gas turbine engines. In addition, measured flame transfer function between the equivalence ratio fluctuation and the heat release fluctuation can be used as direct input to the analytical model to predict combustion instabilities.

Equivalence ratio has been measured using infrared (IR) methane absorption of the 3.39 μm wavelength output of a He—Ne laser to study its effect on heat release during pre-mixed unstable combustion (lab scale). Local fuel-to-air ratio was also measured by laser absorption at the same wavelength to study the effect of mixing on NOx emissions in premixed burner. The same IR laser absorption technique has been also used to measure fuel concentration in pulse detonation engines and internal combustion engines. However, He—Ne lasers are sensitive to ambient conditions and simultaneously emit diffuse radiation and coherent light at multiple discrete wavelengths. In addition, the absorption at 3.39 μm wavelength is the carbon-hydrogen (CH) asymmetric stretch bond common to all hydrocarbon fuels, while different hydrocarbons have different absorption coefficients. Therefore, the sensor needs to be calibrated for each fuel mixture encountered during operation. Thus, the IR absorption method has limitations for practical application in gas turbine engines.

Moreover, the current gas turbine operations rely on overall flow splits to estimate the average flame temperature, and adjust fuel/air ratio for optimal operation in terms of combustion stability and emissions like CO and NOx. However, the capability of this method is limited due to uncertain nozzle-to-nozzle and can-to-can flow variations.

Accordingly, there is an ongoing need for accurately and rapidly measuring an equivalence ratio of the gas-fuel mixture in real time in practical gas turbine engines.

BRIEF DESCRIPTION

In accordance with an embodiment of the invention, a system for a real-time monitoring of an equivalence ratio of a gas-fuel mixture of a gas turbine engine is provided. The system includes multiple optical probes arranged on a plurality of fuel nozzles for transmitting laser beams directly through a gas-fuel mixture or indirectly by reflecting the laser beams from a surface of a centerbody or burner tube of the fuel nozzle. The system also includes one or more detectors to measure the transmitted laser beams from the multiple optical probes. Further, the system includes a data acquisition subsystem for acquiring and processing signals from the one or more detectors to determine the equivalence ratio of the gas-fuel mixture of the nozzle.

In accordance with an embodiment of the invention, a method of monitoring real-time equivalence ratio of a gas-fuel mixture of a gas turbine engine is provided. The method includes transceiving a laser beam through a gas-fuel mixture using a plurality of optical probes arranged on a plurality of fuel nozzles of the engine. The method also includes sensing the transmitted laser beam directly through the gas fuel mixture or indirectly by reflecting from a surface of the fuel nozzle by one or more detectors. The method further includes acquiring detector signals by a data acquisition subsystem. Finally, the method includes processing recorded signals to determine the equivalence ratio of the gas-fuel mixture in real time.

In accordance with an embodiment of the invention, a method of manufacturing a system for a real-time monitoring of an equivalence ratio of a gas-fuel mixture of a gas turbine engine is provided. The method includes providing a tunable diode laser to generate a laser beam with an optimal wavelength for laser absorption measurement. The method also includes providing a plurality of optical probes proximate to a fuel nozzle for transceiving the laser beam directly through a gas-fuel mixture or indirectly by reflecting the laser beam from a surface of the fuel nozzle. The method also includes polishing or painting the surface of the fuel nozzle to increase reflectivity of the laser beam. Further, the method includes providing one or more detectors to measure the laser beams from the optical probes. Finally, the method includes providing a data acquisition subsystem for acquiring and processing the laser signal beam for determining the equivalence ratio of the fuel-air mixture.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed in detail below, embodiments of the invention are directed towards a non-intrusive measurement of an equivalence ratio in gas-fuelled gas turbine engines. As used herein, the phrase 'equivalence ratio' refers to the ratio of the fuel-to-oxidizer ratio to the stoichiometric fuel-to-oxidizer ratio. The present invention addresses a system and method of a real-time monitoring of an equivalence ratio of a gas-fuel mixture of an engine.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Any examples of operating parameters are not exclusive of other parameters of the disclosed embodiments.

Figure 1:
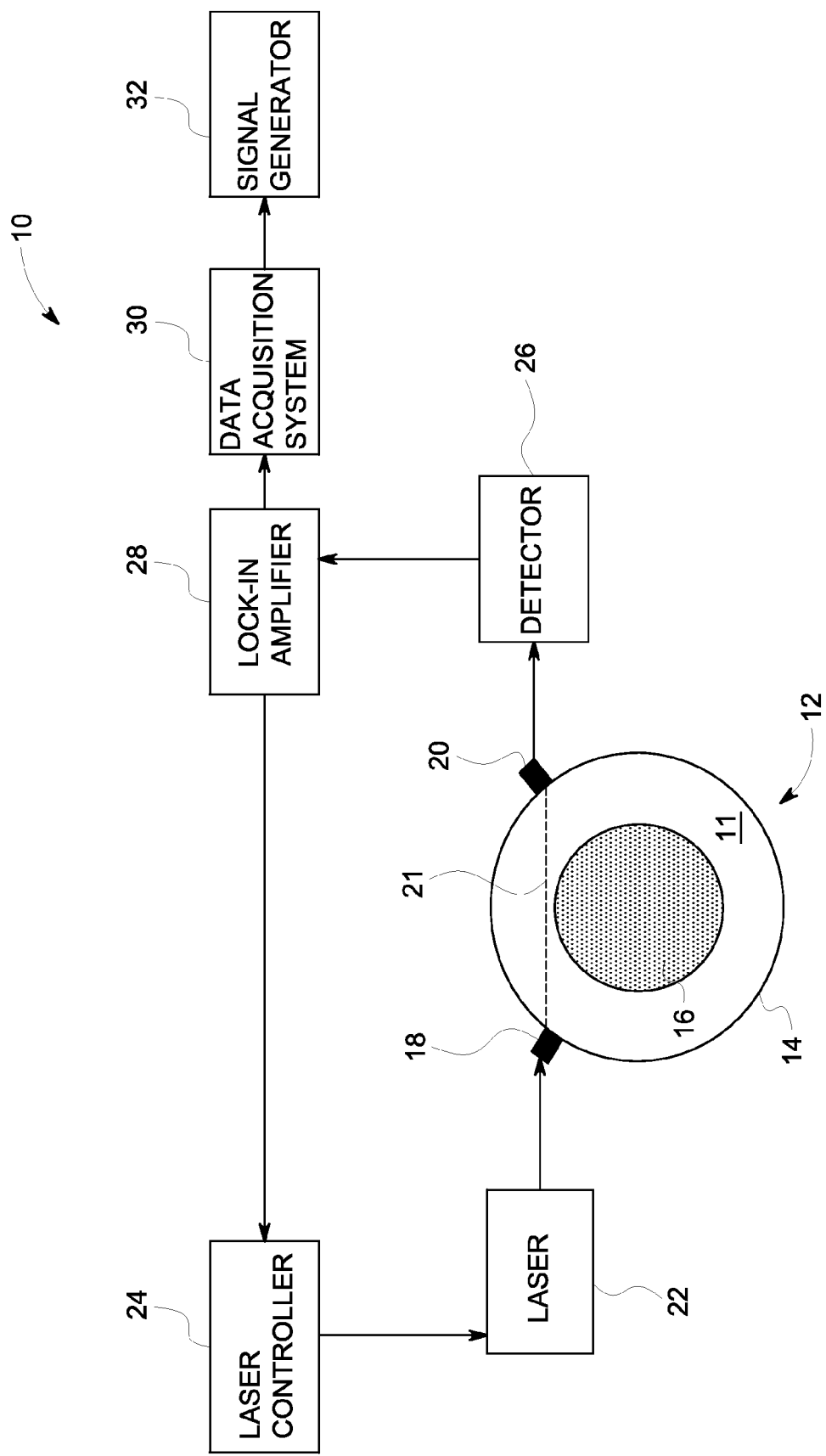
FIG. 1 shows a system for monitoring of an equivalence ratio of a gas-fuel mixture of a gas turbine fuel nozzle in accordance with an embodiment of the present invention.

FIG. 1 shows a sensor system 10 for monitoring of an equivalence ratio of a gas-fuel mixture 11 of an engine combustor in accordance with an embodiment of the present invention. It is to be noted that the sensor system 10 may also be employed to monitor equivalence ratio of gas-fuel mixture and thereby observe combustion conditions of a variety of low-emission, high performing combustion chambers for gas turbines, boilers, heaters and furnaces. A cross-sectional view of the engine combustor 12 is shown having a burner tube 14 and a center-body 16 near the end of the combustor 12 proximate to the flame. The system 10 includes multiple optical probes (18, 20) arranged proximate to the engine nozzle for transceiving signal beams 21 directly through a gas-fuel mixture 11. In one embodiment, the optical probes 18, 20 are fiber-coupled sensor probes mounted on multiple locations on the burner tube 14. The system 10 further includes a tunable diode laser (TDL) 22 for generating the laser beam 21 which is directed through the gas-fuel mixture 11 using one of the optical probes 18 that acts as a laser pitcher. In one embodiment, the TDL 22 is a near infrared TDL to provide an absorption sensor based on fixed wavelength laser absorption of methane near 1.65 micrometer and takes advantage of the large methane mole fraction in unburned gas-fuel mixture. The wavelength range of the laser beam 21 may vary from about 1000 nm to about 4000 nm. As shown, the optical probe 20 acts as a catcher probe and receives the laser beam 21. The system 10 also includes a beam splitter or optical switch for splitting and transmitting the laser beam 21 through the fuel-air mixture of multiple fuel nozzles in the engine. The system 10 further includes a laser controller 24 for modulating the laser wavelength to generate an optimum modulation depth of the laser wavelength. Furthermore, the system 10 includes a laser mount (not shown) for mounting the TDL sensor 22. The system 10 is also configured to have one light path being transmitted through a static cell filled with calibration gas ($CH_4$ and $N_2$ mixture). This calibration of the TDL absorption sensor is carried out to determine the line strength and the laser set point. The system 10 also includes a detector 26 that senses the laser beam 21 and directs the signal to a lock in amplifier 28 for demodulating the sensed signal to simultaneously recover first harmonic (1f) and second harmonic (2f) signals. Thus, the lock in amplifier 28 improves signal to noise ratio and automatically corrects transmission variation due to vibrations or window fouling. In one embodiment, the sensed signal is demodulated by a Perkin-Elmer lock-in amplifier (model 7280) to simultaneously recover the 1f and 2f signals with a time constant of 0.5 milliseconds. In another embodiment, the sensor system 10 bandwidth may be improved by using two lock-in amplifiers or a software lock-in. The sensed signal beam is further processed by a data acquisition (DAQ) system 30. This processing of received signal beams includes using a technique of fixed wavelength modulation spectroscopy (WMS) with second harmonic detection for measuring the real-time equivalence ratio of the fuel-air mixture of a gas turbine engine. The wavelength modulation spectroscopy (WMS) incorporates a transmission coefficient $\tau(v)$ of monochromatic radiation through a uniform gas medium of a engine combustor of length L (cm) given by the Beer-Lambert's law $$\tau(v)=(I_t/I_o)_v=\exp[-P_iS\phi_vL]\approx 1-P_iS\phi_vL, \quad (1)$$

where $I_t$ and $I_o$ are the transmitted and incident laser intensities, S ($cm^{-2}atm^{-1}$) and $\phi_v$ (cm) are the linestrength and lineshape function for the absorption feature, and $P_i$ (atmosphere) is the partial pressure of the absorbing species. The approximation in the right hand side holds for optically thin samples ($P_i S \phi_v L < 0.1$).

In the present invention, the laser wavelength $\nu$ is rapidly modulated with angular frequency $\omega$.

$$\nu(t) = \bar{\nu} + a\cos(\omega t) \quad (2)$$

where $\nu$ (cm$^{-1}$) is the center laser frequency and $a$ (cm$^{-1}$) is the modulation depth. The diode laser intensity is simultaneously modulated.

The transmission coefficient is a periodic even function in $\omega t$ and can thus be expanded in a Fourier cosine series:

$$\tau(\bar{\nu} + a\cos(\omega t)) + \sum_{k=1}^{\infty} H_k(\bar{\nu}, a)\cos(k\omega t), \quad (3)$$

and the second harmonic Fourier component is given by $$H_2(\bar{\nu}, a) = -\frac{S(T)P_i L}{\pi} \int_{-\pi}^{+\pi} \varphi(\bar{\nu} + a\cos\theta)\cos 2\theta d\theta \quad (4)$$

For WMS detection, the lock-in amplifier 28 is used to measure the second-harmonic (2f) signal by multiplying the detector signal by a sinusoidal reference signal at frequency $2\omega$. This technique is sensitive to absorption line shape curvature and is insensitive to low frequency noise. Thus, WMS 2f detection offers benefits over direct absorption in terms of noise resistance and sensitivity. The lock-in amplifier 28 acts as a band-pass filter and rejects noise outside the lock-in bandwidth. In addition, WMS measurements eliminate the need of problematic baseline fitting required in scanned-wavelength direct absorption measurements, especially in the case of weak absorbance. Finally, normalization of the WMS-2f signal with the 1f signal removes the need for calibration and account for the laser transmission variations due to beam steering, scattering, and window fouling. Such normalization is important for practical applications in gas turbine combustor to account for intrinsic laser transmission variations.

In the present invention, the TDL 22 incorporates using the fixed-wavelength WMS with second harmonic detection to simplify data processing and facilitate real-time equivalence ratio measurement. The laser wavelength is set at the line center of the absorption feature to maximize WMS-2f signal.

The measured 2f/1f ratio is directly proportional to the partial pressure of absorption species if the line shape function does not vary with test conditions. When the gas pressure and temperature are measured by a pressure transducer and a thermocouple, then the equivalence ratio is determined from the measured ratio with known fuel composition.

The DAQ system 30 of the present system 10 includes an electronic signal processor that is adapted and configured to analyze and process real-time data received from lock-in amplifier 28 or otherwise directly from detector 26. It should be noted that embodiments of the invention are not limited to any particular processor for performing the processing tasks of the invention. The term "electronic signal processor," as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art. The system 10 also includes a signal generator 32 that generates output signals based upon the data received from the optical probes 18, 20 and processing of the received data by the DAQ system 30.

Figure 2:
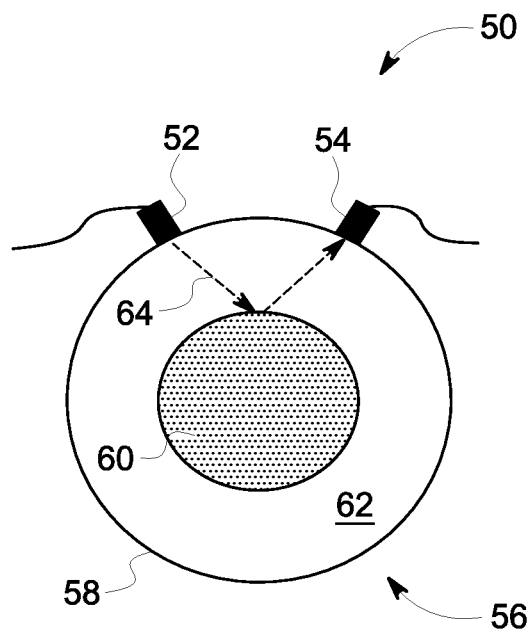
FIG. 2 illustrates a sensor system having an arrangement of multiple optical probes on a burner tube in accordance with an embodiment of the present invention.

FIG. 2 illustrates a sensor system 50 having an arrangement of multiple optical probes 52, 54 on an engine combustor 56 in accordance with an embodiment of the present invention. The system 50 depicts a cross-sectional view of an engine combustor 56 with a burner tube 58 and a center-body 60. The multiple optical probes 52, 54 are arranged circumferentially on the burner tube 58 for transceiving laser beams 64 indirectly through a gas-fuel mixture 62. In this embodiment, the multiple optical probes 52, 54 transceive signal beams 64 indirectly by reflecting the signal beams from a surface of the center body 60 of the fuel nozzle. The first optical probe 52 and the second optical probe 54 are mounted on the burner tube such that the transmitted signal laser beam 60 subtend an optimal angle at the surface of the center-body 60. For high performance of the present system 50, the surface of the center-body 60 may be polished or painted or treated for substantial reflectivity.

Figure 3:
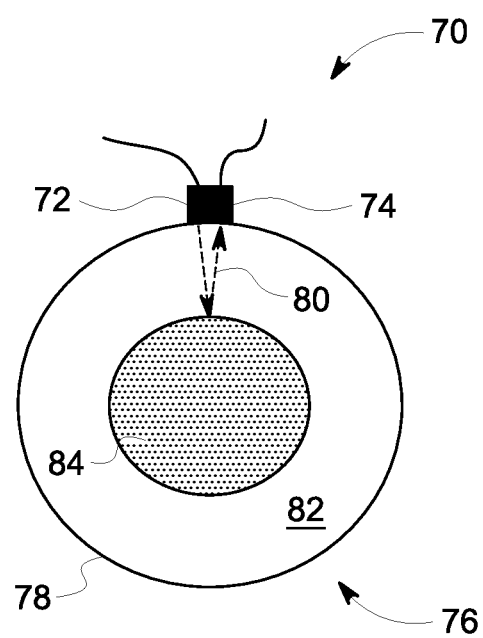
FIG. 3 shows another arrangement of optical probes on a burner tube in accordance with an embodiment of the present invention.

FIG. 3 shows another sensor system 70 having an arrangement of multiple optical probes 72, 74 on an engine combustor 76 in accordance with another embodiment of the present invention. The system 70 depicts a cross-sectional view of an engine combustor 76 with a burner tube 78 and a center-body 84. The first optical probe 72 and the second optical probe 74 are mounted on a burner tube 78 such that both the probes are located adjacent to each other on a single port. The multiple optical probes 72, 74 transceive laser beams 80 indirectly through a gas-fuel mixture 82 by reflecting the laser beams from a surface of the center body 84 of the engine. The second optical probe 74 acts as a catching probe and receives a portion of the laser beam reflected off the surface of the center body 84 of the engine combustor 76.

Figure 4:
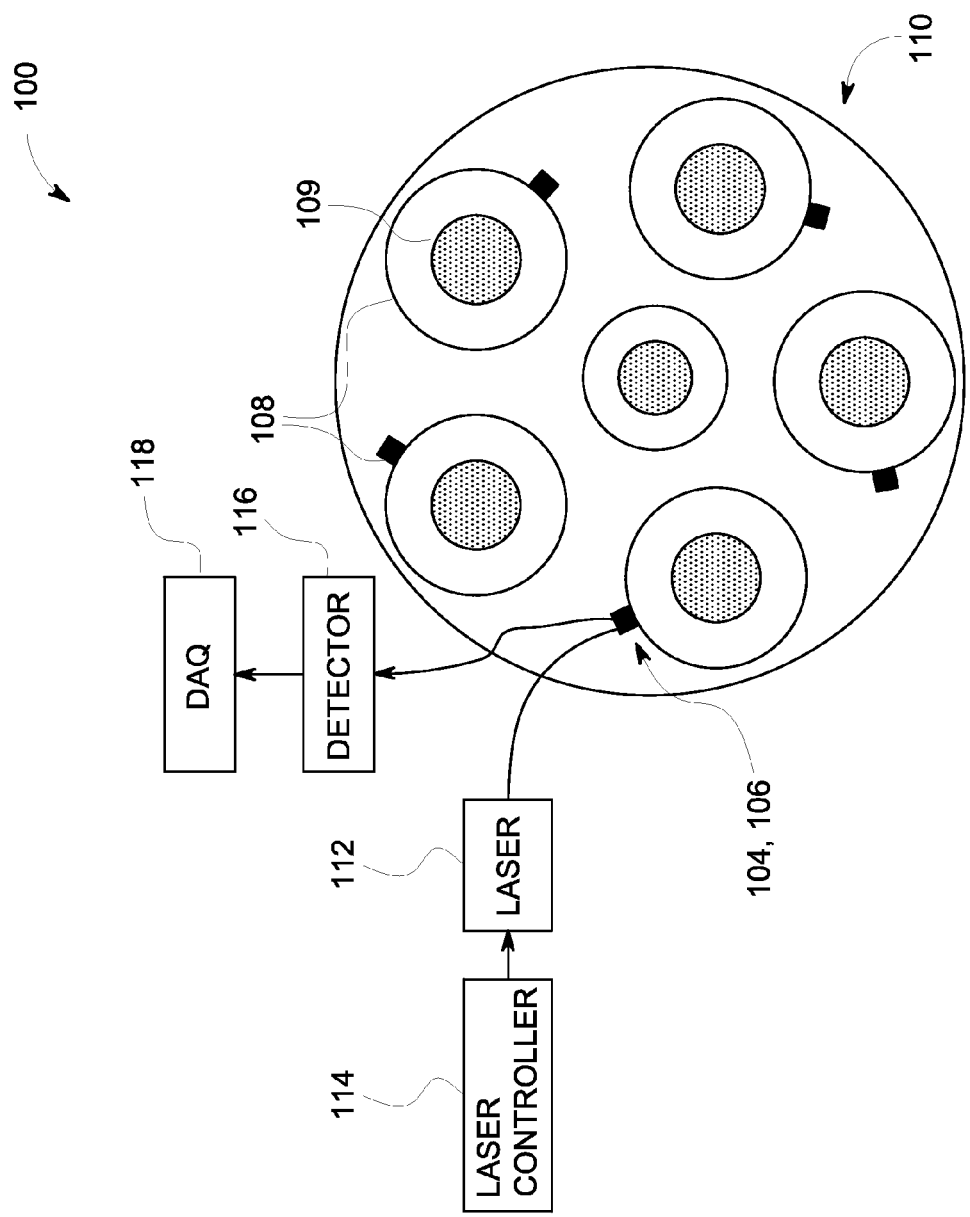
FIG. 4 shows sensor system having an arrangement of multiple optical probes on multiple burner tubes of a gas turbine engine in accordance with an embodiment of the present invention.

FIG. 4 shows sensor system 100 having an arrangement of multiple optical probes 104, 106 on a gas turbine engine 110 in accordance with an embodiment of the present invention. A typical cross-sectional view of a gas turbine 110 is shown having a can that includes multiple nozzles and multiple burner tubes 108 circumferentially shrouding multiple center-bodies 109. As illustrated, multiple optical probes 104, 106 are mounted on one such burner tube for transceiving signal beams indirectly through a gas-fuel mixture by reflecting the signal beams from a surface of the center body of the gas turbine engine 110. It is to be understood that multiple optical probes may be mounted on the multiple burner tubes for monitoring the equivalence ratio proximate to the multiple nozzles of the gas turbine engine 110 simultaneously. In a non-limiting manner, any of the previously discussed embodiments of the various arrangements of optical probes may be used for mounting the probes on the multiple burner tubes in this embodiment. The sensor system 100 also includes a laser device 112 for generating a laser beam that is directed by the optical probe into the gas-fuel mixture of the engine for detecting the equivalence ratio. As shown, a laser controller 114 is configured to modulate the laser wavelength to generate an optimum modulation depth of the laser beam required to measure the equivalence ratio. Further, the sensor system 100 includes a detector 116 that measures the laser signal and directs the signal to a data acquisition system (DAQ) 118. The DAQ 118 processes the received signal to determine the real time equivalence ratio of the gas-fuel mixture in the gas turbine engine 110.

Figure 5:
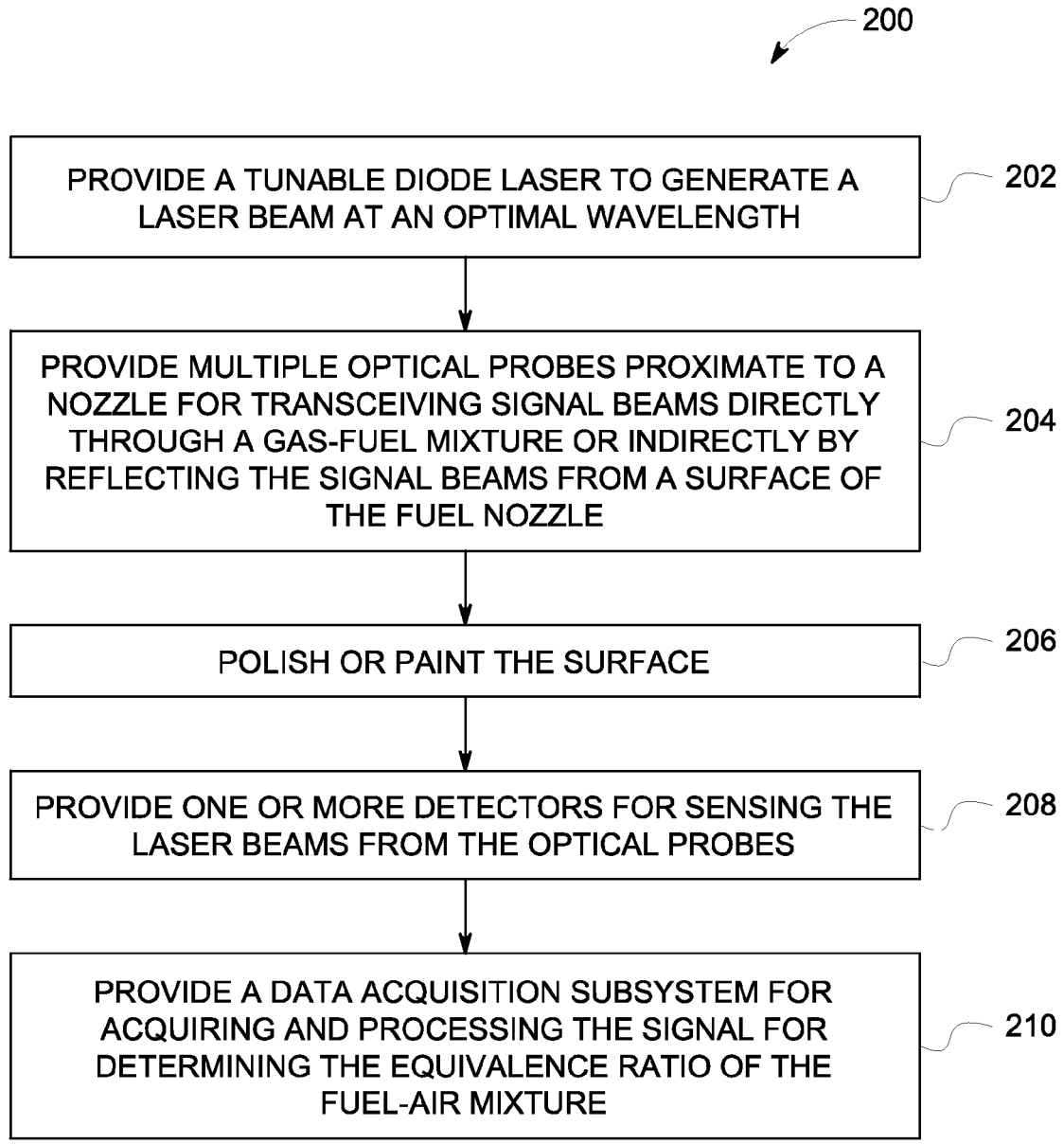
FIG. 5 shows a flow chart of a method of manufacturing a sensor system for a real-time monitoring of equivalence ratio of a gas-fuel mixture of an engine in accordance with an embodiment of the present invention.

FIG. 5 shows a flow chart of a method 200 of manufacturing a sensor system for a real-time monitoring of equivalence ratio of a gas-fuel mixture of an engine in accordance with an embodiment of the present invention. At step 202, the method includes providing a tunable diode laser (TDL) sensor to generate a laser beam at wavelength that is strongly absorbed by gas component in fuel. At step 204, the method includes providing multiple optical probes proximate to a nozzle for transceiving the laser beam directly through a gas-fuel mixture or indirectly by reflecting the laser beam from a surface of the fuel nozzle. Further, at step 206, the method includes polishing or painting the surface of the fuel nozzle. The method also includes providing one or more detectors for sensing the signal beams from the optical probes at step 208. Finally at step 210, the method includes providing a data acquisition subsystem for acquiring and processing the signal beams for determining the equivalence ratio of the fuel-air mixture. The sensor system also includes a signal generator that sufficiently generates output signals showing real-time equivalence ratio as functions of various parameters under multiple conditions in an engine combustor. Further, the method 200 includes providing a laser controller and a lock-in amplifier for demodulating the detector signal for simultaneously recovering first harmonic (1f) and second harmonic (2f) signals to improve signal to noise ratio, automatic transmission correction, and remove the need for calibration. Furthermore, the method 200 also includes providing a beam splitter for splitting the signal beam into a first signal beam and a second signal beam; transmitting the first signal beam through the fuel-air mixture of the gas turbine engine; and transmitting the second signal beam through a static cell for determining a laser setpoint.

Figure 6:
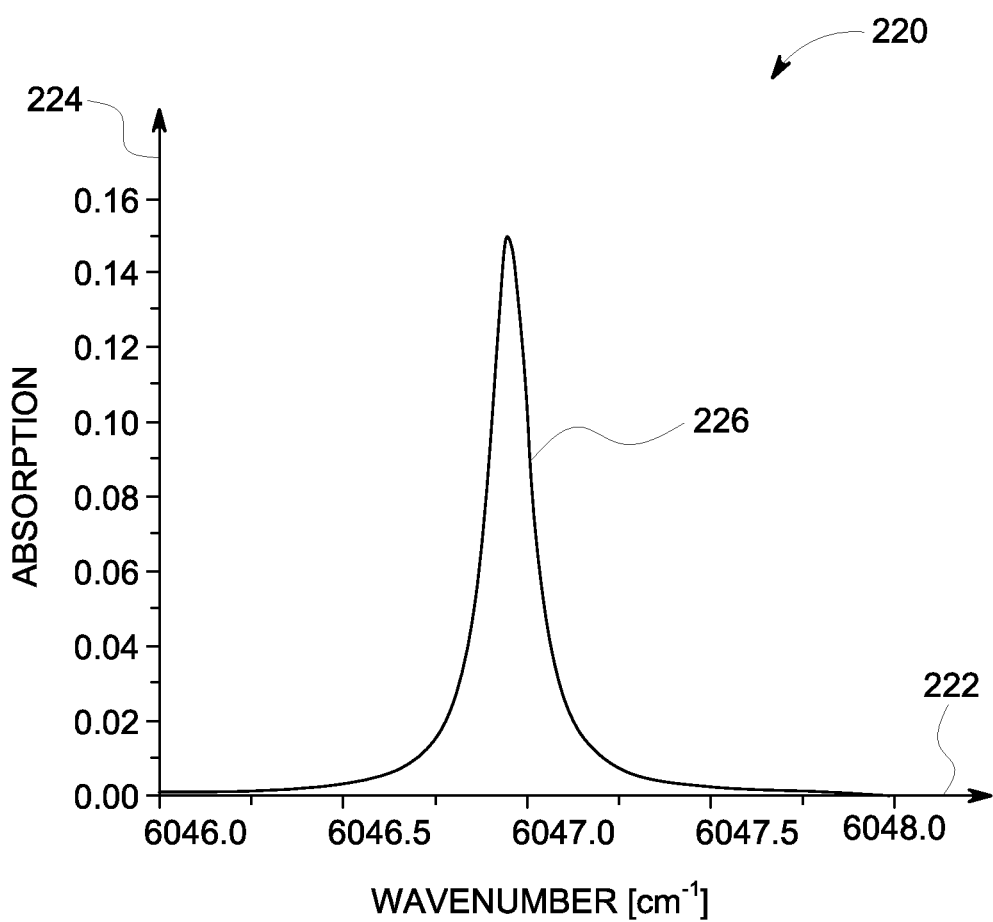
FIG. 6 is a non-limiting example of a graphical representation of a simulated methane absorption spectrum for a typical lean-premixed gas turbine combustor.

By way of a non-limiting example, a graphical representation of a methane absorption spectrum 220 is shown in FIG. 6. The absorption spectrum 220 is simulated for a typical lean premixed gas turbine combustor conditions (pressure of 1 atmosphere, 6% methane in air, gas medium length L=7 cm and temperature=700K). The x-axis 222 represents wavenumber in inverse centimeter ($cm^{-1}$) units. The Y-axis 224 represents absorption. In the present invention, the real time TDL sensor for equivalence ratio is based on near-IR absorption of methane around 1.65 μm (6047 $cm^{-1}$ wavenumber) as shown by the curve 226. There is minimum interference for methane absorption measurements from other species in air. The line around 1653.725 nm is well isolated at atmospheric pressure, and thus is selected for the present TDL sensor.

There are several advantages of the present TDL sensor compared to previous sensors based on infrared (IR) absorption of He—Ne lasers. First, the near-IR fiber-coupled TDL sensor takes advantage of mature technology for distributed-feedback (DFB) telecom diode lasers, near-IR fibers and optics, and thus has much higher signal to noise ratio (SNR). Second, the DFB diode laser output wavelength and power are very stable, and laser wavelength is readily tuned with temperature and injection current. Wavelength modulation spectroscopy is combined with second-harmonic detection to improve the TDL sensor sensitivity and accuracy. Third, the near-IR TDL sensor is not sensitive to transmission loss from window fouling or beam steering by using 1f normalization. The methane ($CH_4$) absorption level at near-IR is more suitable for line-of-sight applications to ensure sufficient transmission and absorption. The absorbance near 1.65 μm stays around 3-4%, which is ideal for WMS-2f measurement.

Figure 7:
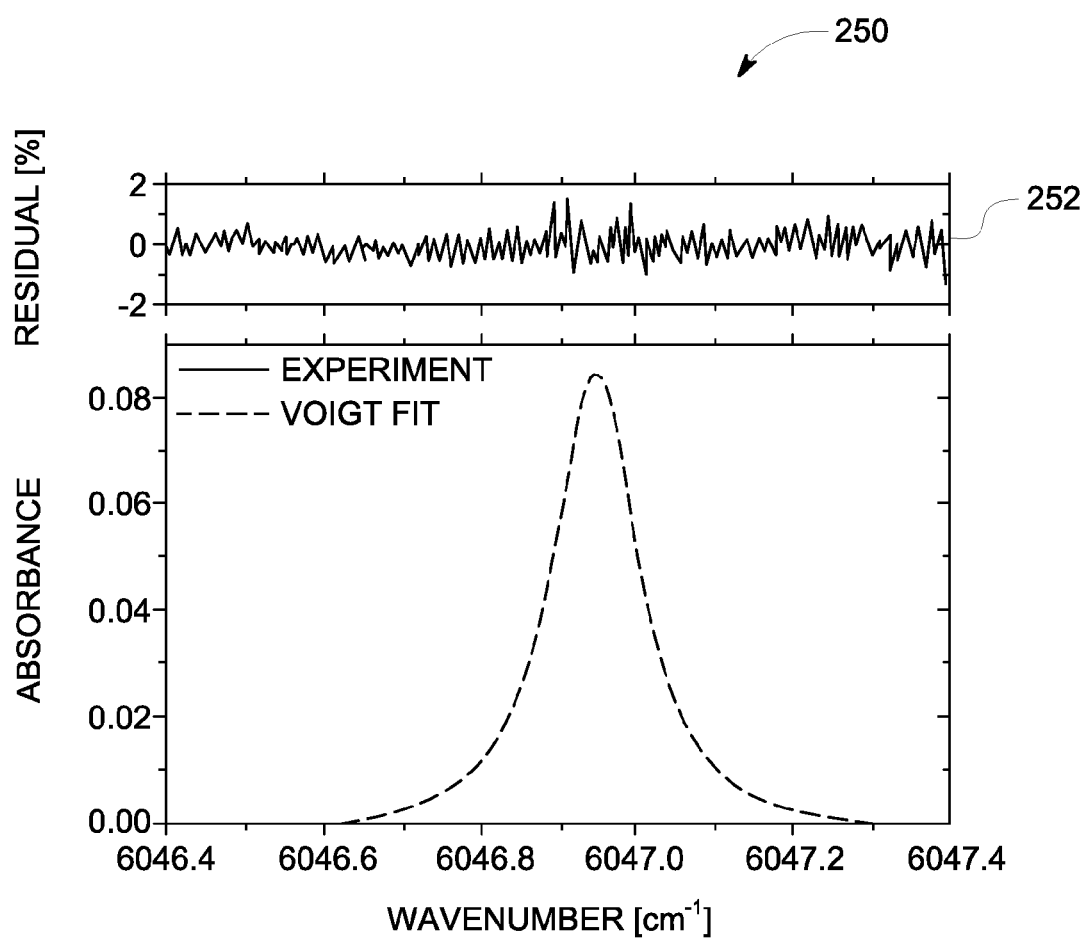
FIG. 7 is a non-limiting example of a graphical representation showing the measured absorption spectrum in a static cell in accordance with an embodiment of the present invention.

Furthermore, in one embodiment, the calibration of the present TDL sensor is carried out in a well controlled environment using a static cell with a mixture of 5.44% $CH_4$ in $N_2$ to determine the linestrength and find the laser setpoint. For direct absorption measurement, the laser wavelength is tuned with a linear current ramp at a frequency of 100 Hz. FIG. 7 is a non-limiting example of a graphical representation 250 showing the measured methane absorption line shape around 1653.725 nm in the static cell (pressure of 1 atmosphere, temperature of 297 K, gas medium length L=4.5 cm) in accordance with an embodiment of the present invention. The experimental profile is best fit using a Voigt profile, and the residual (difference between data and fit normalized by the peak absorbance) is shown in the upper panel 252. The linestrength for this absorption feature can be inferred using the integrated absorbance area.

Figure 8:
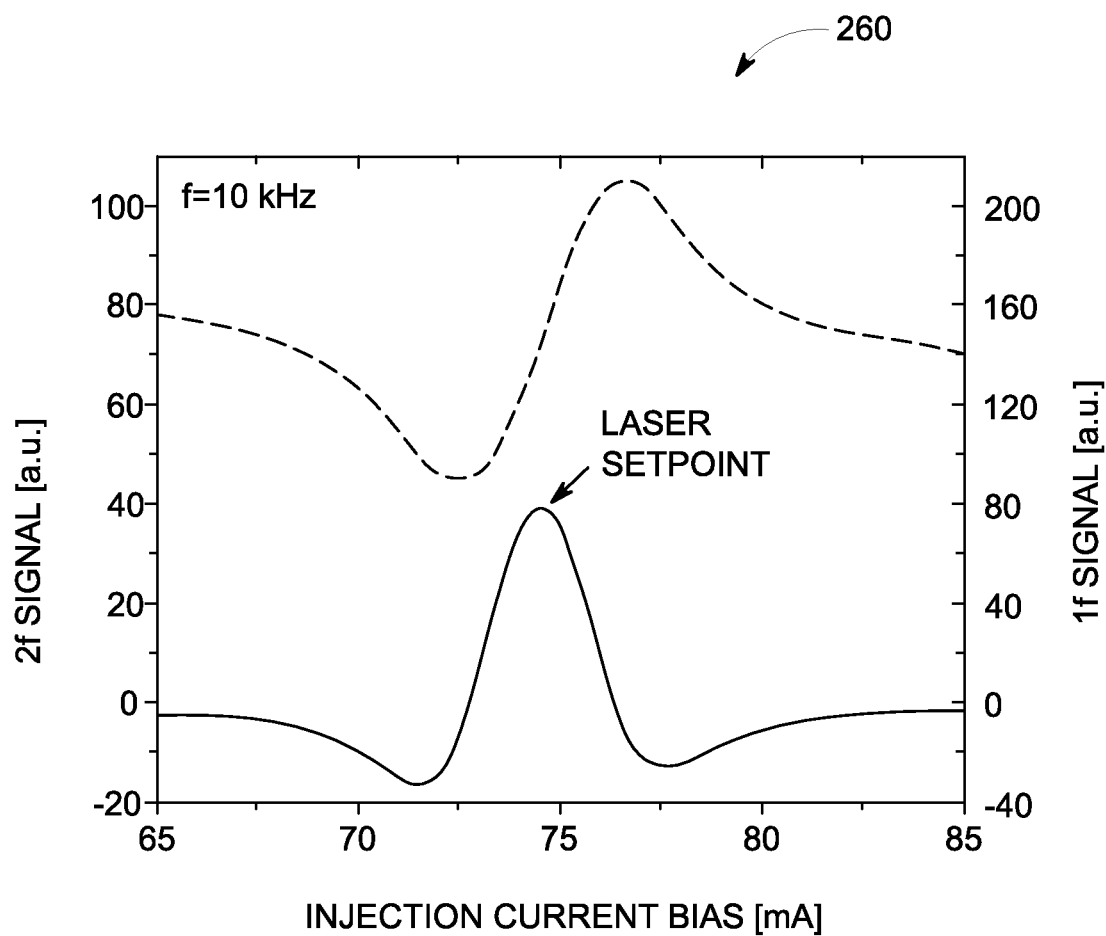
FIG. 8 shows a non-limiting example of a measured WMS-1f and -2f spectra when the injection bias current is varied in accordance with an embodiment of the present invention.

For WMS measurement, the laser wavelength is sinusoidally modulated. FIG. 8 shows a non-limiting example of the measured WMS-1f and -2f spectra when the injection bias current is varied from 65 to 85 miliampere (mA) in accordance with an embodiment of the present invention. The 1f signal has a large offset due to amplitude modulation. Since the 2f signal peaks at the absorption line center, the laser wavelength can be locked by maximizing the 2f signal for fixed-wavelength WMS measurement. This process is repeated before each combustion test to ensure correct laser setpoint.

Figure 9:
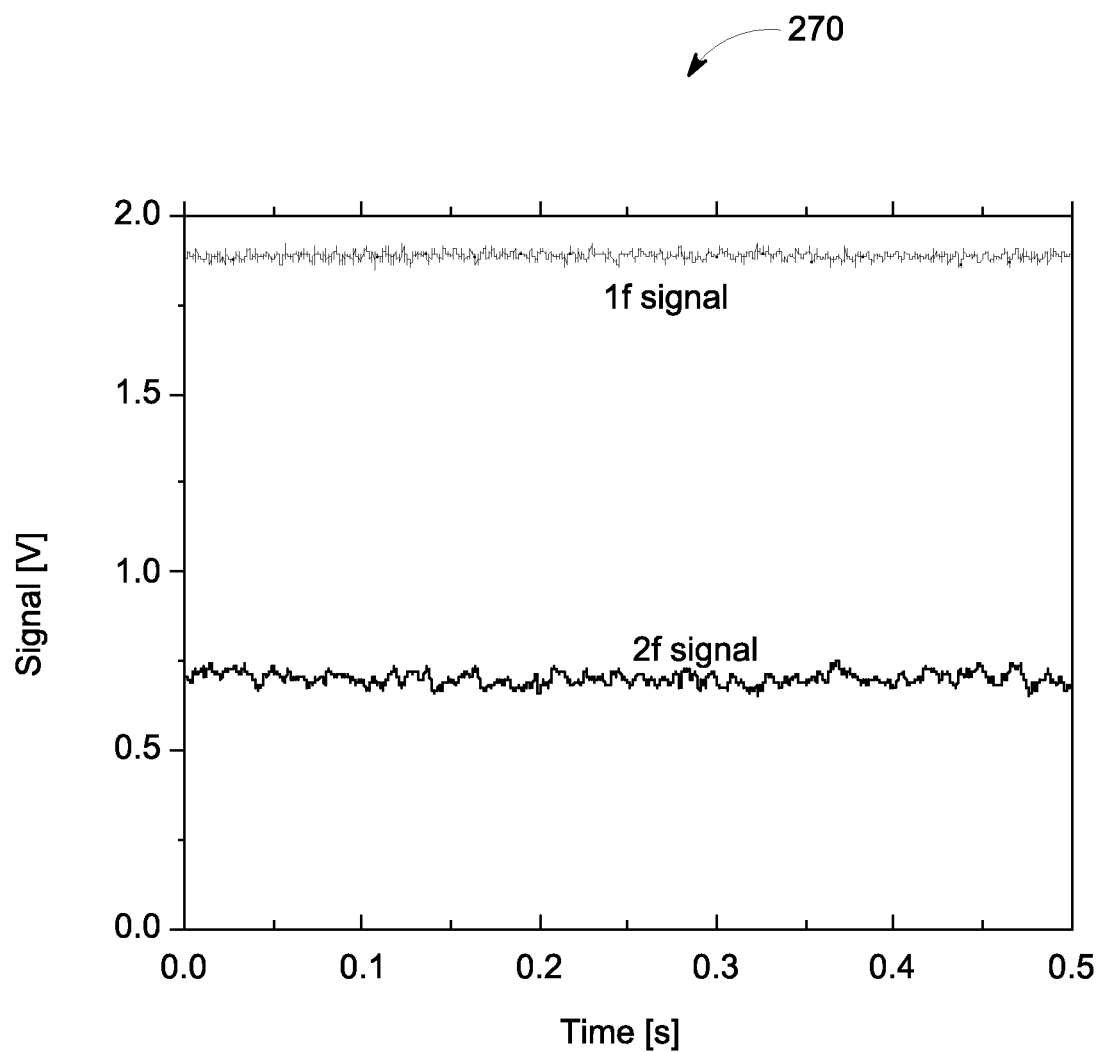
FIG. 9 is a non-limiting example of a graphical representation showing a measured wavelength mean spectroscopy (WMS) first harmonic (1f) and second harmonic (2f) signals for steady conditions in accordance with an embodiment of the present invention.
Figure 10:
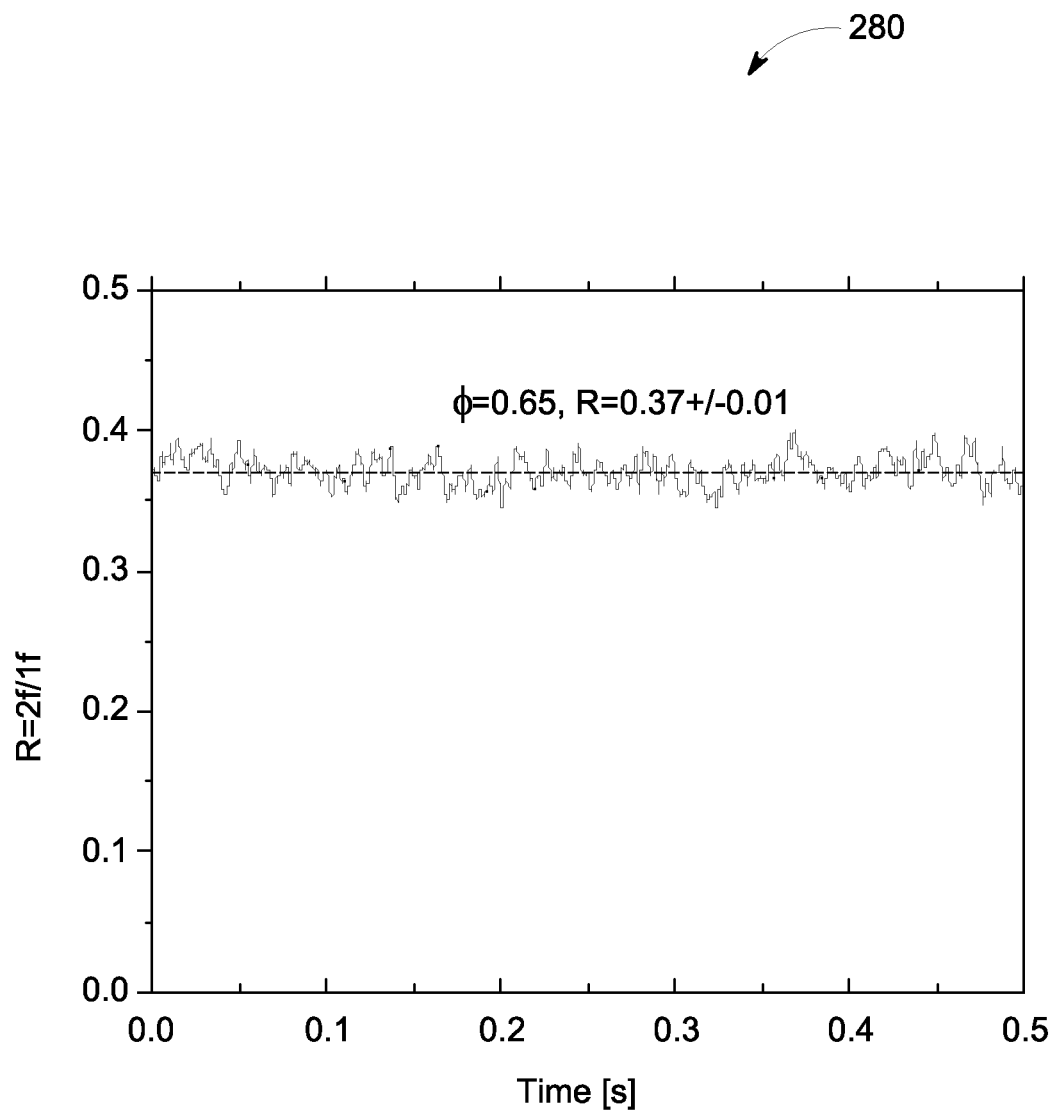
FIG. 10 shows a non-limiting example of a measured ratio of second harmonic (2f) signal and first harmonic (1f) signal for steady conditions in accordance with an embodiment of the present invention.
Figure 11:
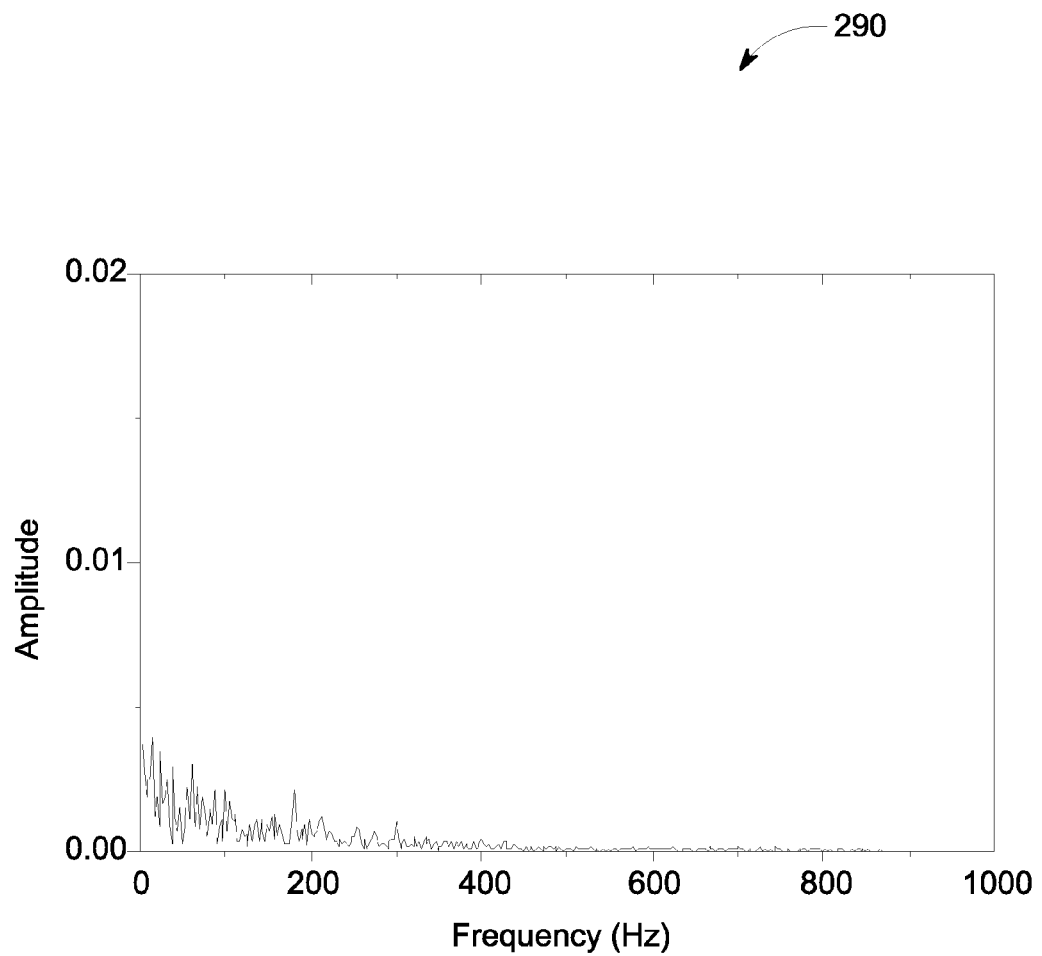
FIG. 11 shows a non-limiting example of a fast Fourier transform (FFT) spectrum for steady conditions in accordance with an embodiment of the present invention.

By way of another non-limiting example, FIG. 9 shows a graphical representation 270 of a measured WMS-1f and -2f signals under steady conditions in accordance with an embodiment of the present invention. A time resolution of 0.5 ms is achieved for the TDL sensor with a lock-in time constant of 0.5 ms. The measured ratio 280 as shown in FIG. 10, is not steady, probably due to unsteady turbulent mixing. FIG. 11 shows non-limiting example of a fast Fourier transform (FFT) spectrum of data 290 for steady conditions. No distinct frequency is found on the FFT spectrum, indicating random equivalence ratio fluctuation along the sensor line-of-sight.

Figure 12:
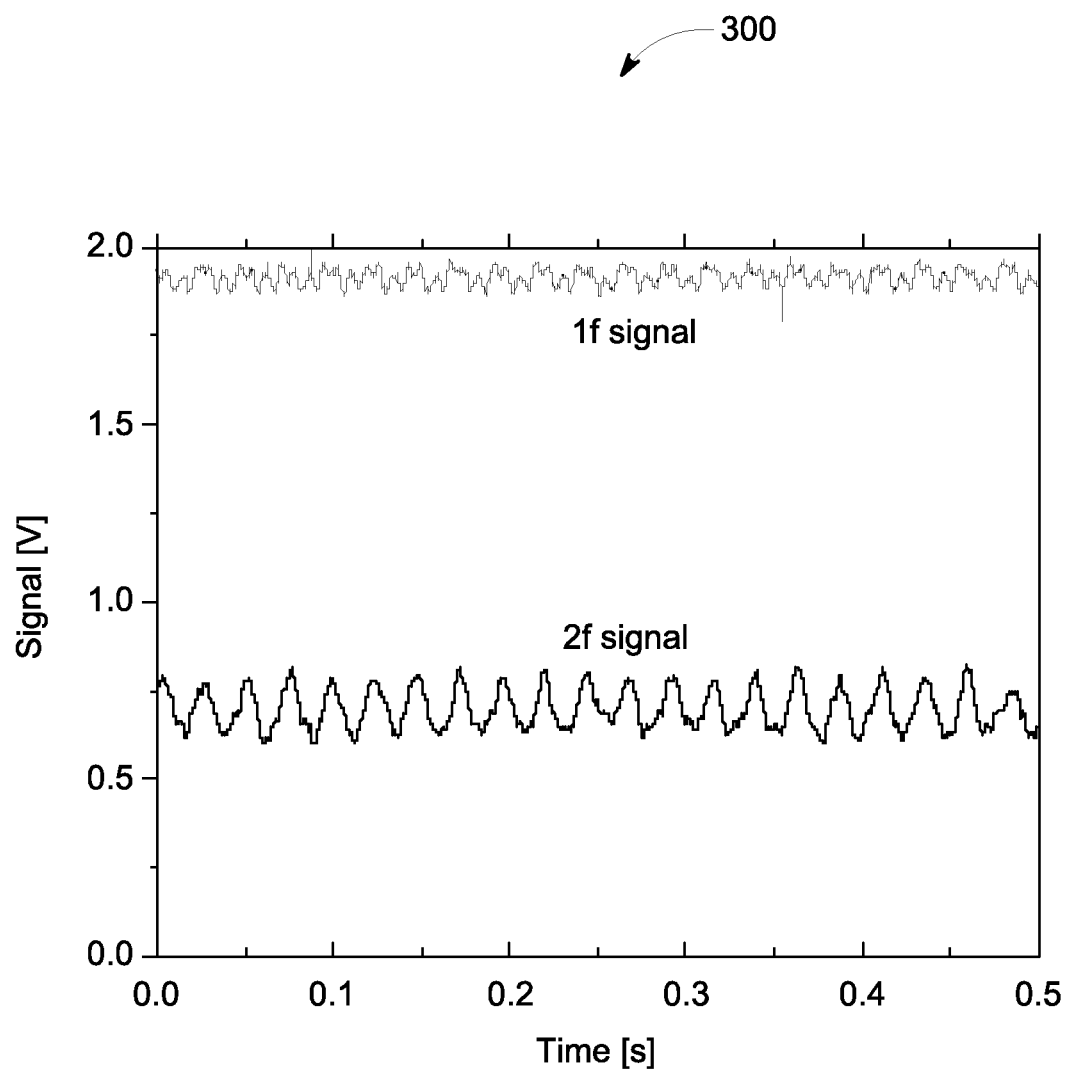
FIG. 12 is a non-limiting example of a graphical representation showing a measured WMS-1f and -2f signals for forced flame conditions in accordance with an embodiment of the present invention.
Figure 13:
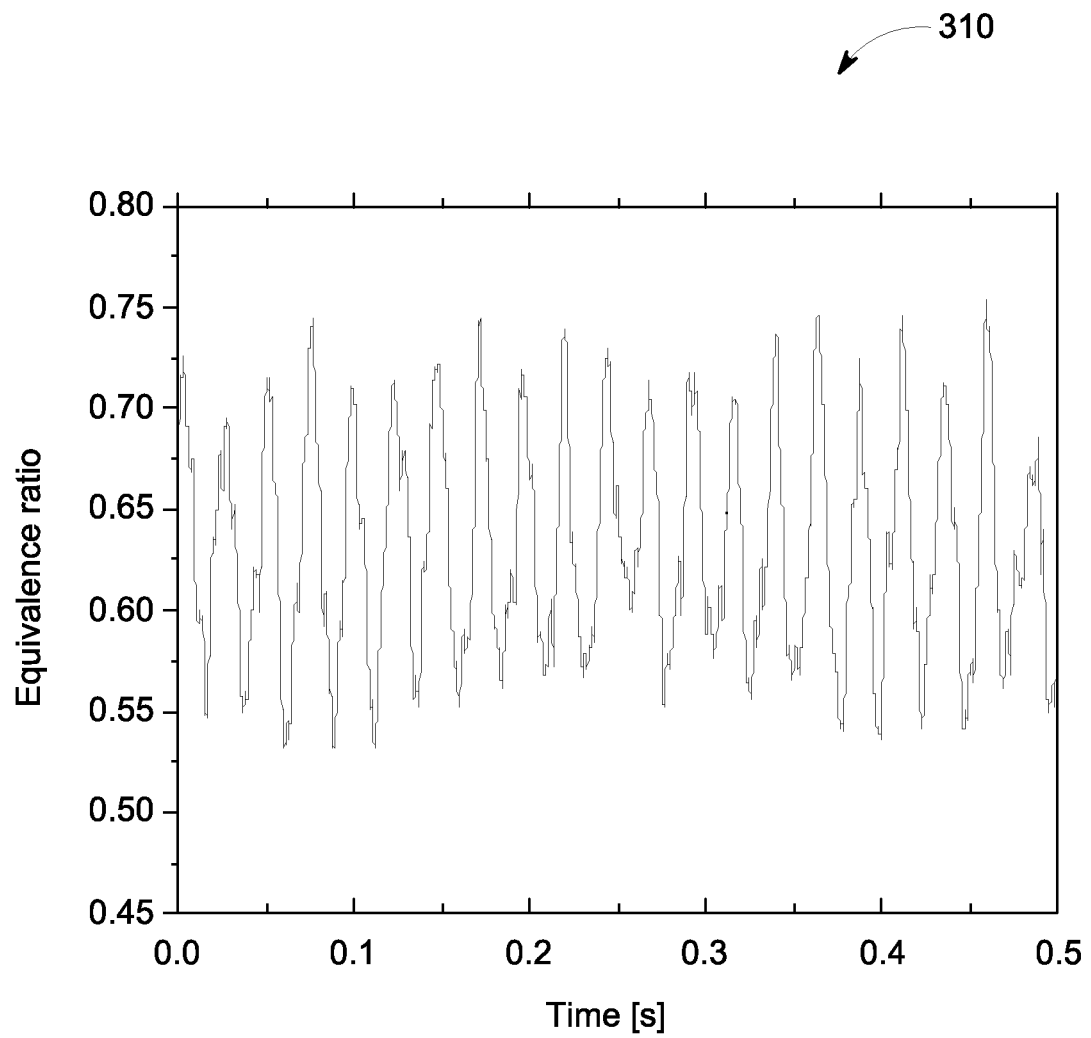
FIG. 13 shows a non-limiting example of measured equivalence ratio for forced flame conditions in accordance with an embodiment of the present invention.
Figure 14:
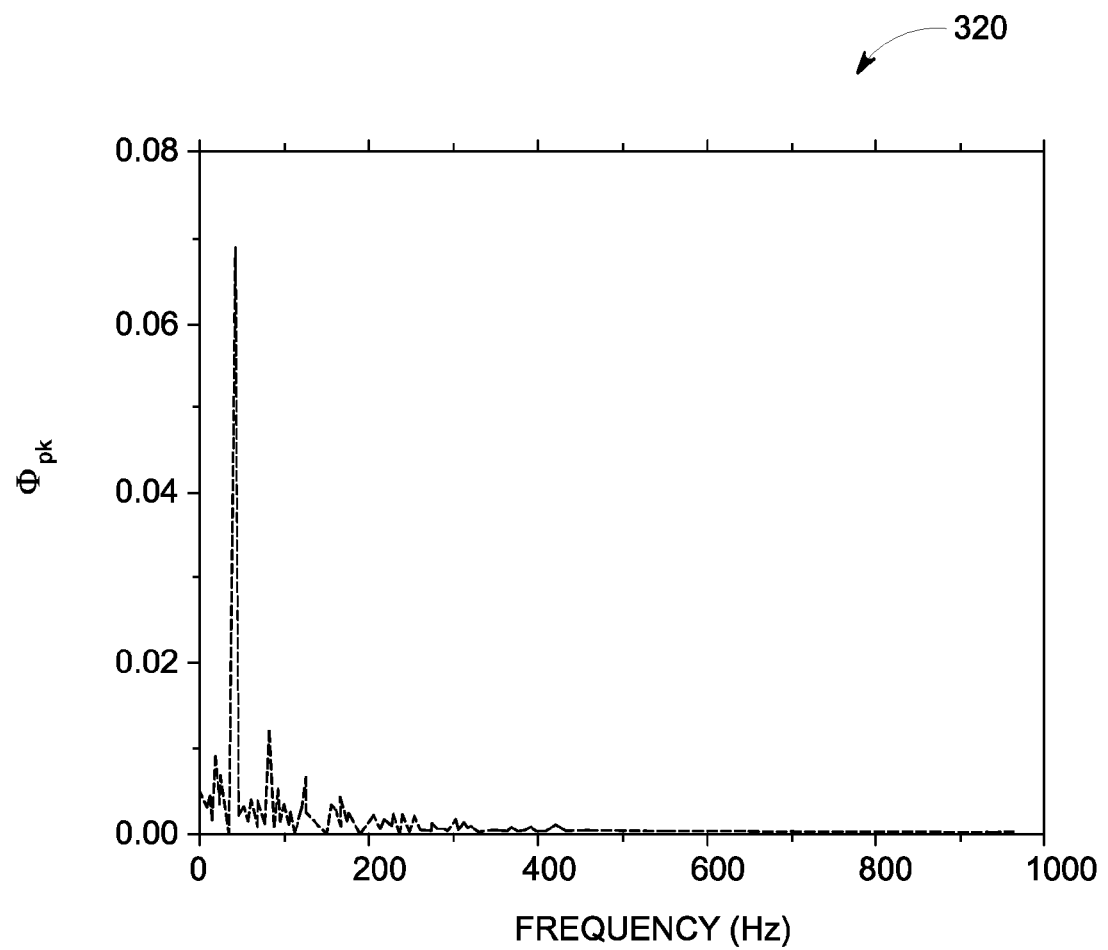
FIG. 14 shows a non-limiting example of a fast Fourier transform (FFT) spectrum for forced flame conditions in accordance with an embodiment of the present invention.

By way of a non-limiting example, FIG. 12 shows a non-limiting example of a graphical representation 300 of a measured WMS-1f and -2f signals for air flow of 0.177 kg/s and inlet air temperature of 297 K under forced flame conditions. In this non-limiting example, the fuel flow rate is constant, so the equivalence ratio near combustor exit is changing due to varying airflow rate. FIG. 12 illustrates the measured time history of WMS-1f and 2f signals for the forcing frequency of 42 Hz (mean φ=0.63). It can be seen from the 1f signal that the laser transmission signal is fluctuating, probably due to the vibrations of windows and test rig. This result clearly demonstrates the advantage of the TDL sensor with automatic laser transmission correction using 1f normalization. FIG. 13 and FIG. 14 shows non-limiting examples of measured equivalence ratio 310 and a fast Fourier transform (FFT) spectrum 320 for the forced flame. The dominant oscillation mode (42 Hz) and the harmonics can be clearly seen from the FFT spectrum. The zero-to-peak equivalence ratio oscillation of the fundamental mode is about 0.069. Without 1f-normalization, the peak equivalence ratio oscillation would be 0.075 (9% higher than actual value). This result demonstrates that the rapid TDL sensor can be used to accurately characterize equivalence ratio fluctuations in gas turbine combustor.

Figure 15:
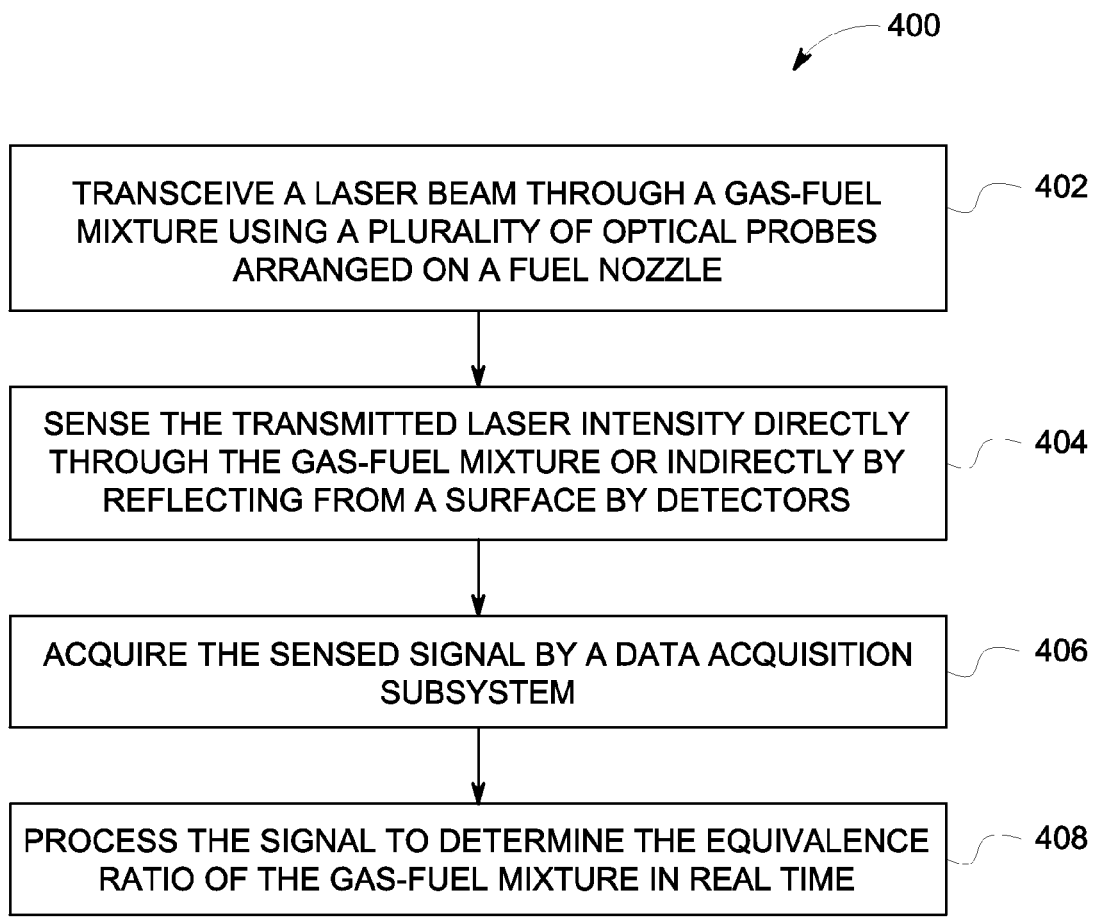
FIG. 15 shows a flow chart of a method of monitoring real-time equivalence ratio of a gas-fuel mixture of an engine in accordance with an embodiment of the present invention.

FIG. 15 shows a flow chart of a method 400 of monitoring real-time equivalence ratio of a gas-fuel mixture of an engine in accordance with an embodiment of the present invention. At step 402, the method includes transceiving a signal beam through a gas-fuel mixture using a plurality of optical probes arranged proximate to a fuel nozzle of the engine. The signal beams are laser beams generated by a rapid near infrared tunable diode laser (TDL). The method also includes calibrating the TDL absorption sensor to determine line strength and a laser setpoint. As shown in FIG. 1, the optical probe 18 is mounted on the burner tube of the engine combustor and transmits a laser beam through the gas-fuel mixture to another optical probe 20. At step 404, the method includes sensing the signal beam transmitted directly through the gas-fuel mixture or indirectly by reflecting from a surface of the nozzle by one or more detectors (shown as detector 26 in FIG. 1). The sensed signal beam is further acquired by a data acquisition subsystem (DAQ system 30 as shown in FIG. 1) at step 406. Prior to the step 406, the sensed signal beams are modulated by a lock in amplifier. Finally at step 408, the method 400 includes processing the signal to determine the equivalence ratio of the gas-fuel mixture in real time.

Advantageously, the present method and system enables direct measurement of gas-fuel ratio for each turbine combustor in real-time, and thus provides the flame temperature directly. In-situ real time measurement of gas-fuel ratio (and its fluctuation) can provide valuable information for combustor optimization and control, especially for gas turbine engines with multiple nozzles in a combustion can. In addition, this method can provide online data to monitor part-to-part and engine-to-engine component variations. In addition, this invention also provides practical sensor arrangement for gas turbine applications. Thus, the present invention provides sensor for real time active control of gas turbine combustors to optimize efficiency and reliability. For example, a real-time equivalence ratio data can be used to control firing temperature to improve engine efficiency. In the case of combustion dynamics with equivalence ratio fluctuation, this real-time information can provide feedback control signal for the active control system to suppress instabilities.

Furthermore, the skilled artisan will recognize the interchangeability of various features from different embodiments. Similarly, the various method steps and features described, as well as other known equivalents for each such methods and feature, can be mixed and matched by one of ordinary skill in this art to construct additional systems and techniques in accordance with principles of this disclosure. Of course, it is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for a real-time monitoring of an equivalence ratio of a gas-fuel mixture of a gas turbine engine, the system comprising:
    a plurality of optical probes arranged on a plurality of fuel nozzles for transmitting laser beams directly through a gas-fuel mixture or indirectly by reflecting the laser beams from a surface of a center body or burner tube of the fuel nozzle; wherein the plurality of optical probes comprises a first optical probe and a second optical probe mounted circumferentially or axially on the burner tube such that the laser beams transmitted between the first optical probe and the second optical probe after reflection from the surface of the fuel nozzle follows a pathway that subtends an optimal angle at the surface;
    one or more detectors for receiving the transmitted laser beams from the plurality of optical probes; and
    a data acquisition subsystem for acquiring and processing signals from the one or more detectors, using a technique of a fixed wavelength modulation spectroscopy (WMS) with a second-harmonic signal detection, for determining the equivalence ratio of the gas-fuel mixture of the gas turbine engine in real time.

2. The system of claim 1, further includes a plurality of laser devices, a plurality of controllers and the plurality of optical probes for directing laser beams through the gas-fuel mixture in the fuel nozzles.

3. The system of claim 1, wherein the plurality of optical probes are arranged on burner tubes of the fuel nozzles, wherein the fuel nozzles are mounted on an annular combustion chamber or in a combustor can of the gas turbine engine.

4. The system of claim 1, wherein the plurality of optical probes comprise fiber-coupled sensor probes mounted on a plurality of locations on the burner tube.

5. The system of claim 1, wherein the first optical probe is configured to transmit the laser beam through the gas-fuel mixture or onto a surface of the fuel nozzle, wherein the fuel nozzle comprises the center body or the burner tube.

6. The system of claim 1, wherein the second optical probe is configured to receive the laser beam transmitted directly through the gas-fuel mixture or indirectly by reflection from the surface of the fuel nozzle.

7. The system of claim 1, wherein the first optical probe and the second optical probe are located adjacent to each other on the burner tube.

8. The system of claim 2, wherein the plurality of laser devices are based on near infrared or mid-infrared lasers.

9. The system of claim 1, wherein the wavelength of the laser beam ranges from about 1000 nm to about 4000 nm.

10. The system of claim 2, wherein one of the laser devices comprise a rapid near infrared tunable diode laser (TDL) for absorption measurement.

11. The system of claim 1, further comprising a lock-in amplifier for measuring a first-harmonic and a second-harmonic signals to improve signal to noise ratio.

12. The system of claim 11, wherein the data acquisition subsystem is configured to normalize the second-harmonic signals with the first-harmonic signals to automatically correct transmission variation due to vibrations or window fouling.

13. A method of monitoring a real-time equivalence ratio of a gas-fuel mixture of a gas turbine engine, the method comprising:
    transceiving a laser beam through a gas-fuel mixture using a plurality of optical probes arranged proximate to a plurality of fuel nozzles of the engine;
    transmitting the laser beams between a first optical probe and a second optical probe among the plurality of optical probes, after reflection from a surface of the fuel nozzle along a pathway that subtends an optimal angle at the surface; wherein the first optical probe and the second optical probe are mounted circumferentially or axially on the burner tube;
    sensing the laser beam transmitted directly through the gas-fuel mixture or indirectly by reflecting from a surface of the fuel nozzle by one or more detectors;
    acquiring detector signals by a data acquisition subsystem; and processing recorded signals using a technique of a fixed wavelength modulation spectroscopy (WMS) with a second-harmonic signal detection to determine the equivalence ratio of the gas-fuel mixture in real time.

14. The method of claim 13, further comprising calibrating a tunable diode laser for determining a line strength and a laser set point.

15. A method of manufacturing a system for a real-time monitoring of an equivalence ratio of a gas-fuel mixture of a gas turbine engine, comprising:
providing a tunable diode laser to generate a laser beam with an optimal wavelength for absorption measurement;
providing a plurality of optical probes proximate to a fuel nozzle among the plurality of fuel nozzles for transceiving the laser beam directly through a gas-fuel mixture or indirectly by reflecting the laser beam from a surface of the fuel nozzle; wherein providing the plurality of optical probes comprises mounting a first optical probe and a second optical probe circumferentially or axially on a burner tube of the fuel nozzle such that the laser beam transmitted between the first optical probe and the second optical probe, after reflection from the surface of the fuel nozzle follows a pathway that subtends an optimal angle at the surface;
polishing or painting the surface of the fuel nozzle to improve reflectivity for the laser beam;
providing one or more detectors for detecting the laser beams from the optical probes; and
providing a data acquisition subsystem for acquiring and processing the signals from the one or more detectors, using a technique of a fixed wavelength modulation spectroscopy (WMS) with a second-harmonic signal detection, for determining the equivalence ratio of the gas-fuel mixture in real time.

16. The method of claim 15, further comprising providing a laser controller and a lock-in amplifier for demodulating the detector signal for simultaneously recovering a first-harmonic (1f) and a second-harmonic (2f) signals to improve signal to noise ratio.

17. The method of claim 15, further comprising: providing a beam splitter for splitting the signal beam into a first signal beam and a second signal beam; transmitting the first signal beam through the gas-fuel mixture of the gas turbine engine; and transmitting the second signal beam through a static cell for determining a laser set point.

18. A system for a real-time monitoring of an equivalence ratio of a gas-fuel mixture of a gas turbine engine, the system comprising:
a plurality of optical probes arranged on a plurality of fuel nozzles for transmitting laser beams directly through a gas-fuel mixture or indirectly by reflecting the laser beams from a surface of a center body or burner tube of the fuel nozzle;
a beam splitter for splitting and transmitting the laser beams through the gas-fuel mixture of the plurality of fuel nozzles;
one or more detectors for receiving the transmitted laser beams from the plurality of optical probes; and
a data acquisition subsystem for acquiring and processing signals from the one or more detectors, using a technique of a fixed wavelength modulation spectroscopy (WMS) with a second-harmonic signal detection, for determining the equivalence ratio of the gas-fuel mixture of the gas turbine engine in real time.

19. A method of monitoring real-time equivalence ratio of a gas-fuel mixture of a gas turbine engine, the method comprising:
transceiving a laser beam through a gas-fuel mixture using a plurality of optical probes arranged proximate to a plurality of fuel nozzles of the engine; wherein transceiving comprises splitting and transmitting the laser beam through the gas-fuel mixture of the plurality of fuel nozzles via a beam splitter;
sensing the laser beam transmitted directly through the gas-fuel mixture or indirectly by reflecting from a surface of the fuel nozzle by one or more detectors;
acquiring detector signals by a data acquisition subsystem; and
processing recorded signals using a technique of a fixed wavelength modulation spectroscopy (WMS) with a second-harmonic signal detection to determine the equivalence ratio of the gas-fuel mixture in real time.

20. A method of manufacturing a system for a real-time monitoring of an equivalence ratio of a gas-fuel mixture of a gas turbine engine, comprising:
providing a tunable diode laser to generate a laser beam with an optimal wavelength for absorption measurement;
providing a plurality of optical probes proximate to a fuel nozzle among the plurality of fuel nozzles for transceiving the laser beam directly through a gas-fuel mixture or indirectly by reflecting the laser beam from a surface of the fuel nozzle;
providing a beam splitter for splitting and transmitting the laser beam through the gas-fuel mixture of the fuel nozzle;
polishing or painting the surface of the fuel nozzle to improve reflectivity for the laser beam;
providing one or more detectors for detecting the laser beams from the optical probes; and
providing a data acquisition subsystem for acquiring and processing the signals from the one or more detectors, using a technique of a fixed wavelength modulation spectroscopy (WMS) with a second-harmonic signal detection, for determining the equivalence ratio of the gas-fuel mixture in real time.

21. The method of claim 16, comprising providing the data acquisition subsystem for normalizing the second-harmonic (2f) signals with the first-harmonic (1f) signals to automatically correct transmission variation due to vibrations or window fouling.

* * * * *